US007985561B2

(12) United States Patent
Ambs et al.

(10) Patent No.: US 7,985,561 B2
(45) Date of Patent: Jul. 26, 2011

(54) MANGANESE SUPEROXIDE DISMUTASE VAL16ALA POLYMORPHISM PREDICTS RESISTANCE TO CHEMOTHERAPEUTIC DRUG CANCER THERAPY

(75) Inventors: Stefan Ambs, Silver Spring, MD (US); Brenda Boersma, Hagerstown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 135 days.

(21) Appl. No.: 12/268,655

(22) Filed: Nov. 11, 2008

(65) Prior Publication Data

US 2009/0136952 A1    May 28, 2009

Related U.S. Application Data

(63) Continuation-in-part of application No. PCT/US2007/000685, filed on May 9, 2007.

(60) Provisional application No. 60/799,788, filed on May 11, 2006.

(51) Int. Cl.
*G01N 33/574* (2006.01)

(52) U.S. Cl. .............................. 435/7.23; 435/6; 435/7.1

(58) Field of Classification Search .......................... None
See application file for complete search history.

(56) References Cited

FOREIGN PATENT DOCUMENTS

WO    WO 01//75175 A2    10/2001
WO    WO 2006/012361 A2    2/2006

OTHER PUBLICATIONS

Slaughter et al, PNAS, 1981, 78:1124-1128.*
Campbell, General Properties and Applications of Monoclonal Antibodies, pp. 1-32, in Monoclonal Antibody Technology, 1984, Elsevier Science Publishers.*
Bergman et al, J Cancer Res Clin Oncol, 2005, 131:439-444.*
Wang et al, Eur J Canver, 2009, 45:2874-2881.*
Busken, C et al, Digestive Disease Week Abstracts and Itinerary Planner, 2003, abstract No: 850.*
Krontiris and Capizzi, Internal Medicine, 4th Edition, Editor-in-chief Jay Stein, Elsevier Science, 1994 Chapters 71-72, pp. 699-729.*
Tockman et al, Cancer Res., 1992, 52:2711s-2718s.*
Kaiser, Science, 2006, 313, 1370.*
Ambrosone et al., "Manganese Superoxide Dismutase (*MnSOD*) polymorphism and breast cancer in a population-based case-control study," 1999, Cancer Research, 59, 602-606.
Ambrosone et al., "Polymorphisms in Genes Related to Oxidative Stress (*MPO, MnSOD, CAT*) and Survival After Treatment for Breast Cancer," 2005, Cancer Res., 65, 3, 1105-1111.
Beck et al., "Human Mn superoxide dismutase cDNA sequence," 1987, Nucleic Acid Research, vol. 15, No. 21, 9076.

Bergman et al., "Polymorphism in the manganese superoxide dismutase (MnSOD) gene and risk of breast cancer in young women," 2005, J. Cancer Res. Clin. Oncol., 131(7), 439-444.
Egan et al., "MnSOD polymorphism and breast cancer in a population-based case-control study," 2003, Cancer Lett., 199(1): 27-33.
Green et al., "Variation in the manganese superoxide dismutase gene (SOD2) is not a major cause of radiotherapy complications in breast cancer patients," 2002, Radiotherapy and Oncology, 63, 213-216.
Hecki, "Isolation of cDNAs encoding human manganese superoxide dismutase," 1988, Nucleic Acids Research, vol. 16, No. 13, 6224.
Hiroi et al.,"Polymorphisms in the SOD2 and HLA-DRB1 genes are associated with nonfamilial idiopathic dilated cardiomyopathy in Japanese," 1999, Biochem Biophys Res. Commun., 261(2), 332-339.
Hur et al., "Manganese Superoxide Dismutase Expression Correlates with Chemosensitivity in Human Gastric Cancer Cell Lines," 2003, vol. 9, 5768-5775.
International Preliminary Report dated Nov. 20, 2008, received in related International Application No. PCT/US2007/068588, filed May 9, 2007.
International Search Report dated Apr. 12, 2007, received in related International Application No. PCT/US2007/068588, filed May 9, 2007.
Kamatani et al., "Polymorphic mutations of the Mn-SOD gene in intact human lymphocytes and oral squamous cell carcinoma cell lines," 2003, Biochem. Cell Biol., 81(1), 43-50.
Martin et al., "No apparent association between genetic polymorphisms (-102 C>T) and (-9 T>C) in the human manganese superoxide dismutase gene and gastric cancer(1).," 2005, J. Surg. Res., 124(1), 92-97.
Mitrunen et al., "Association between manganese superoxide dismutase (MnSOD) gene polymorphism and breast cancer risk," 2001, Carcinogenesis, vol. 22, No. 5, pp. 827-829.
Rosenblum et al., "On signal sequence polymorphisms and diseases of distribution," 1996, Proc. Natl. Acad. Sci. , vol. 93, pp. 4471-4473.
Stoehlmacher et al., "The -9Ala/-9Val polymorphism in the mitochondrial targeting sequence of the manganese superoxide dismutase gene (MnSOD) is associated with age among Hispanics with colorectal carcinoma," 2002, Oncol. Rep., 9(2), 235-238.
Suresh et al., "Overexpression of manganese superoxide," 2003, British Journal of Haematology, 120, 457-463.
Sutton et al., "The Ala16Val genetic dimorphism modulates the import of human manganese superoxide dismutase into rat liver mitochondria," 2003, Pharmacogenetics, 13(3), 145-157.
Sutton et al., "The manganese superoxide dismutase Ala16Val dimorphism modulates both mitochondrial import and mRNA stability," 2005, Pharmacogenet Genomics, 15(5), 311-319.
Tamimi et al., "Manganese Superoxide Dismutase Polymorphism, Plasma Antioxidants, Cigarette Smoking, and Risk of Breast Cancer," 2004, Cancer Epidemiol Biomarkers Prev., 13(6), 989-996.

(Continued)

*Primary Examiner* — Misook Yu
*Assistant Examiner* — Mark Halvorson
(74) *Attorney, Agent, or Firm* — Kilpatrick Townsend & Stockton LLP

(57) ABSTRACT

The present invention provides, for the first time, the finding that the manganese superoxide dismutase Val16Ala polymorphism is significantly associated with prognosis for cancer patients treated with chemotherapeutic drug therapy. The alanine allele is a novel biomarker that predicts poor response and poor outcome to chemotherapeutic drug cancer therapy. Conversely, the valine allele predicts a good response and a good outcome to chemotherapeutic drug cancer therapy. Therefore, a genotype assay can be used to determine which alleles a subject is carrying, and subsequently this information can be used to determine if chemotherapeutic drug therapy is appropriate, and to customize therapy according to the patient's MnSOD genotype.

22 Claims, 10 Drawing Sheets

OTHER PUBLICATIONS

Valenti et al., "The mitochondrial superoxide dismutase A16V polymorphism in the cardiomyopathy associated with hereditary haemochromatosis," 2004, J. Med. Genet., 41, 946-950.

Wang et al., "Asbestos exposure, manganese superoxide dismutase (MnSOD) genotype, and lung cancer risk," 2004, J. Occup. Environ. Med., 46(6), 556-564.

Written Opinion dated Nov. 20, 2008, received in related International Application No. PCT/US2007/068588, filed May 9, 2007.

Yen, et al., "The protective role of manganese superoxide dismutase against adriamycin-induced acute cardiac toxicity in transgenic mice," 1996, J. Clin. Invest., vol. 98, No. 5, 1253-1260.

\* cited by examiner

Fig. 1

Manganese superoxide dismutase nucleic acid sequence (SEQ ID NO:1)

```
  1 cgccggcgc gcaggagcgg cactcgtggc tgtggtggct tcggcagcgg cttcagcaga
 61 tcggggcat cagcggtacg accagcacta gcagcatgtt gagccggca gtgtgcggca
121 ccagcaggca gctggctccg gctttggggt atctgggctc caggcagaag cacagcctcc
181 ccgacctgcc ctacgactac ggcgccctgg aacctcacat caacgcgcag atcatgcagc
241 tgcaccacag caagcaccac ggcgcctacg tggagatgtta cagcccagac gaacgtcacc gaggagaagt
301 accaggaggc gttggtcat ggcaaag ggagatgtta cagcccagac agctcttcag cctgcactga
361 agttcaatgg tggtgtcat atcaatcata gcatttttctg gacaaacctc agccctaacg
421 gtggtggaga acccaaaggg gagttgctgg aagccatcaa acgtgactttt ggttcctttg
481 acaagtttaa ggagaagctg acggctgcat ctgttggtgt ccaaggctca ggttggggtt
541 ggcttggttt caataaggaa cggggacact tacaaattgc tgcttgtcca aatcaggatc
601 cactgcaagg aacaacaggc cttattccac tgctggggat tgatgtgtgg gagcacgctt
661 actaccttca gtataaaaat gtcaggcctg attatctaaa agctattttgg aatgtaatca
721 actgggagaa tgtaactgtt aagaatcgaa agatacatgg cttgcaaaaa gtaaaccacg atcgttatgc
781 tgagtatgtt aagctcttta tgactgtttt tttcttgatg taagtggta tagagtactg cagaatacag
841 taagctgctc tattgtagca ttttgtgatg ttgcttagtc acttattatca taaacaactt
901 aatgttctga ataatttctt actaaacatt ttgttattgg gcaagtgatt gaaaatagta
961 aatgcttgt gtgattg
```

Manganese superoxide dismutase amino acid sequence (SEQ ID NO:2)

```
  1 mlsravcgts rqlapalgyl gsrqkhslpd lpydygalep hinagimqlh hskhhaayvn
 61 nlnvteekyq ealakgdvta qtalqpalkf ngghinhsi fwtnlspngg gepkgellea
122 ikrdfgsfdk fkekltaasv gvqgsgwgwl gfnkerghlq iaacpnqdpl qgttglipll
181 gidvwehayy lqyknvrpdy lkaiwnvinw envterymac kk
```

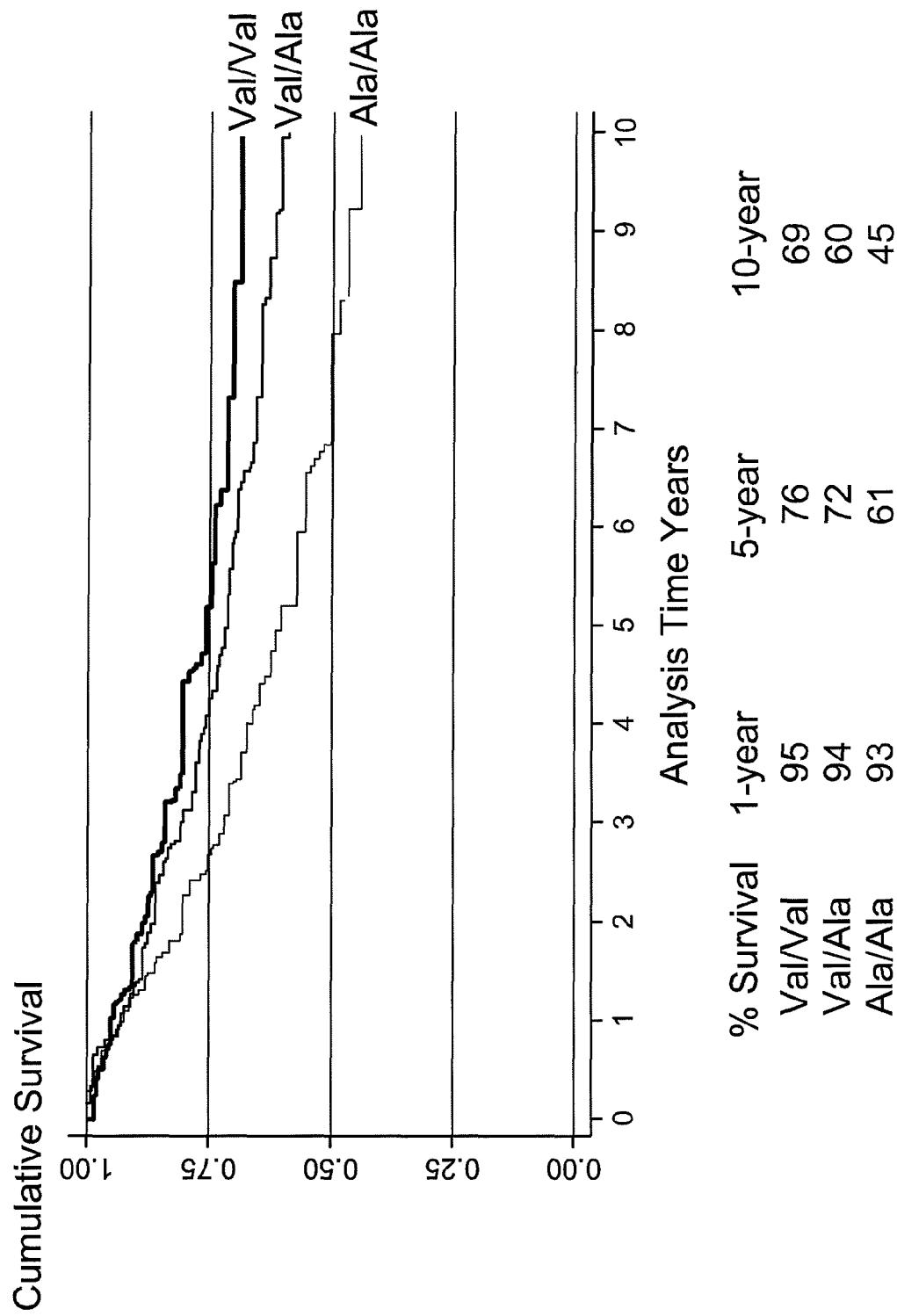

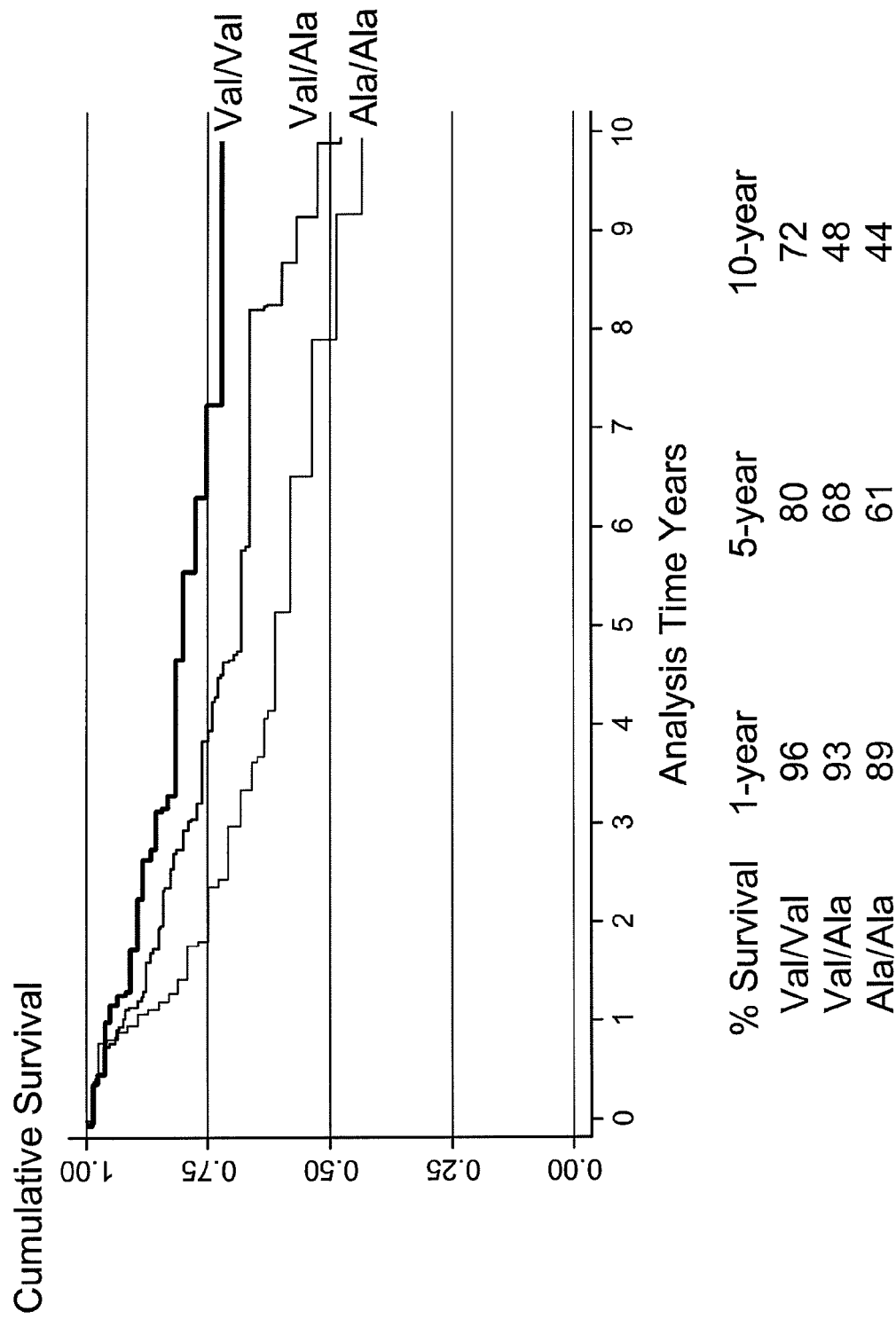

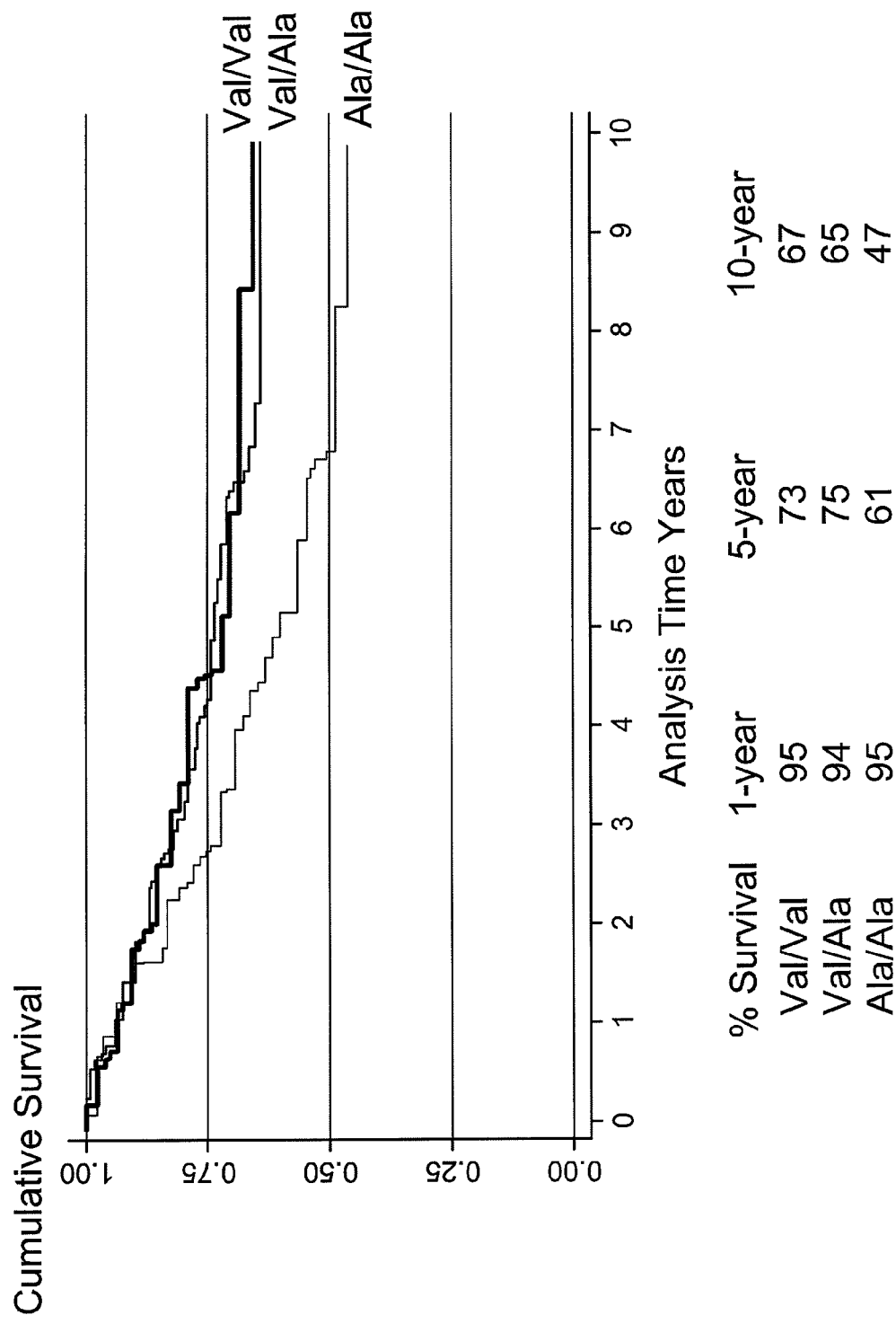

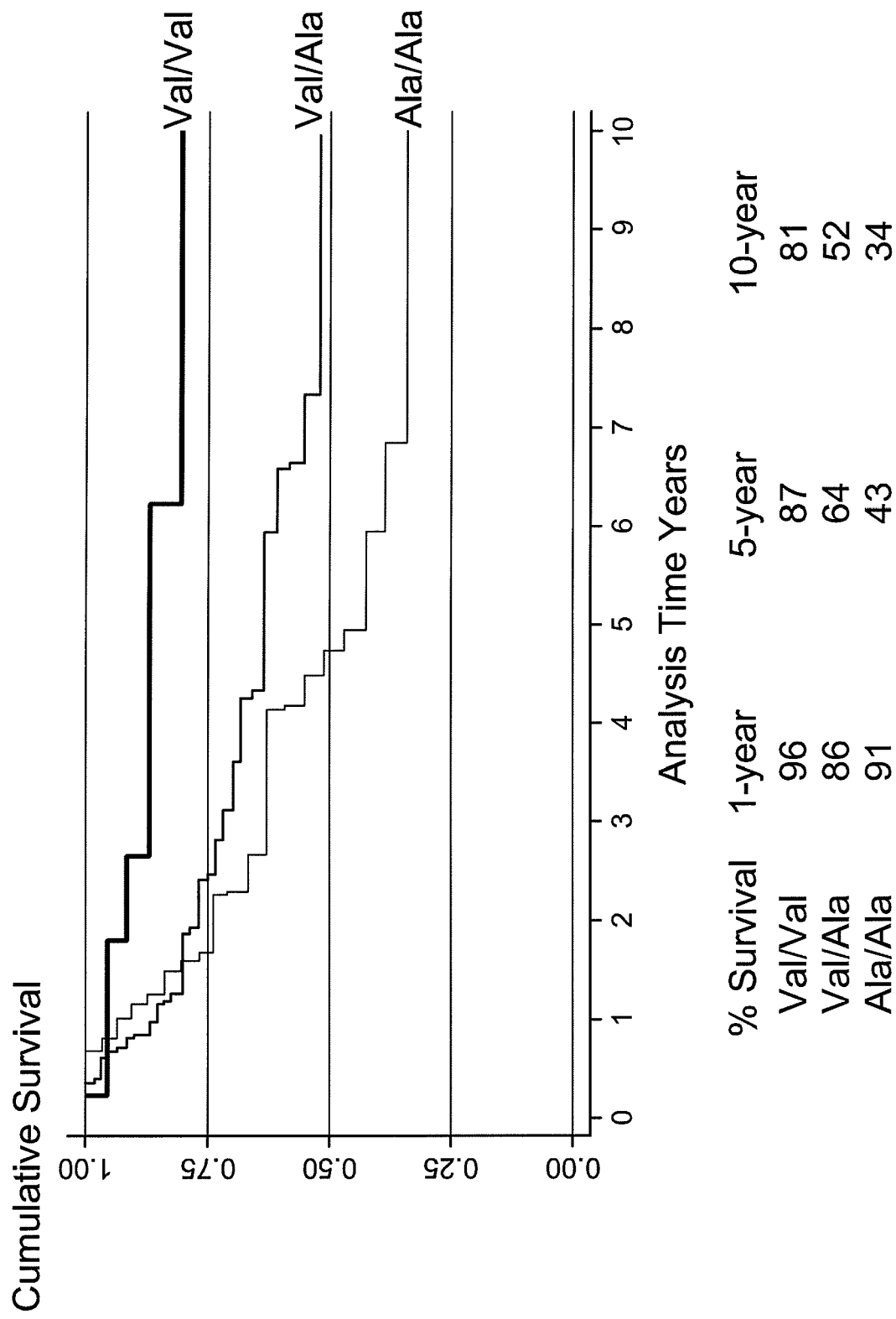

MANGANESE SUPEROXIDE DISMUTASE VAL16ALA POLYMORPHISM PREDICTS RESISTANCE TO CHEMOTHERAPEUTIC DRUG CANCER THERAPY

CROSS-REFERENCES TO RELATED APPLICATIONS

This application is a continuation-in-part of and claims priority to International Application PCT/US2007/068588, with an international filing date of May 9, 2007. The present application also claims priority to U.S. Ser. No. 60/799,788, filed May 11, 2006, herein incorporated by reference in its entirety.

STATEMENT AS TO RIGHTS TO INVENTIONS MADE UNDER FEDERALLY SPONSORED RESEARCH OR DEVELOPMENT

Not applicable

BACKGROUND OF THE INVENTION

Cancer is the second leading cause of death behind heart disease. In fact, cancer incidence and death figures account for about 10% of the U.S. population in certain areas of the United States (National Cancer Institute's Surveillance, Epidemiology, and End Results (SEER) database and Bureau of the Census statistics; see, Harrison's Principles of Internal Medicine, Kasper et al., 16th ed., 2005, Chapter 66). The five leading causes of cancer deaths among men are lung cancer, prostate cancer, colon and rectum cancer, pancreatic cancer, and leukemia. The five leading causes of cancer deaths among women are lung cancer, breast cancer, colon cancer, ovarian cancer, and pancreatic cancer. When detected at locally advanced or metastatic stages, no consistently curative treatment regimen exists. Treatment for metastatic cancer includes immunotherapy, hormonal ablation, radiation therapy, chemotherapy, hormonal therapy, and combination therapies.

Cyclophosphamide (Cytoxan) is a widely used anti-cancer chemotherapy drug and standard agent to treat many cancers, including breast cancer. Cyclophosphamide is an alkylating agent that is metabolically activated by being converted into phosphoramide mustard and acrolein. These active metabolites slow the growth of cancer cells by preventing cell division in a cell-cycle phase-nonspecific manner (see, e.g., Moore, Clin. Pharmacokinet., vol. 20, 194-208, 1991).

5-fluorouracil (fluorouracil) is an anti-cancer chemotherapy drug that is used to treat several types of cancers, including breast cancer. 5-fluorouracil is a pro-drug that is converted to an active drug by metabolism. The active metabolites primarily function by inactivating thymidylate synthase, causing DNA damage which induces cell cycle arrest and apoptosis of cancer cells (see, e.g., Peters et al., Biochim. Biophys. Acta, vol. 1587, 194-205, 2002).

Doxorubicin (adriamycin) is a widely used anti-cancer chemotherapy drug and a standard agent to treat many cancers, including breast cancer. The drug targets topoisomerase II and causes DNA damage. Doxorubicin also targets mitochondria and causes oxidative stress. This latter mechanism is thought to account for both therapeutic efficacy and systemic toxicity. It has been shown that overexpression of manganese superoxide dismutase (MnSOD), an antioxidant enzyme with mitochondrial localization, protects against doxorubicin toxicity and makes cancer cells resistant to doxorubicin treatment (see, e.g., Hur et al., Clin Cancer Research, vol. 9, 5768-5775, 2003; Suresh et al., British J Haematology, vol. 120, 457-463, 2003; Yen et al., J Clin Invest., vol. 98, 1253-1260, 1996).

BRIEF SUMMARY OF THE INVENTION

The present invention provides, for the first time, the finding that the MnSOD Val16Ala polymorphism is significantly associated with prognosis for cancer patients treated with a chemotherapeutic drug. The present invention demonstrates for the first time that the alanine allele is a novel biomarker that predicts poor response and poor outcome to doxorubicin cancer therapy, cyclophosphamide cancer therapy, and 5-fluorouracil cancer therapy, either alone or in combination. Conversely, the valine allele predicts a good response and a good outcome to doxorubicin cancer therapy, cyclophosphamide cancer therapy, and 5-fluorouracil cancer therapy. Therefore, a genotype assay can be used to determine which alleles a subject is carrying, and subsequently this information can be used to determine if chemotherapeutic drug therapy is appropriate, and to customize therapy according to the patient's MnSOD genotype. The patient's genotype can determined by analyzing nucleic acid, e.g., by mass spectroscopy, PCR, sequencing, microarrays, or using an antibody probe. The patient's genotype can also be determined by analyzing protein, e.g., by mass spectroscopy or antibody probe. In one embodiment, a blood sample is used for genotyping. The methods of the invention can be used to predict therapy outcome and prognosis, as well as to determine choice of therapy, for any cancer treated with chemotherapeutic drugs.

In one aspect, the present invention provides a method of providing a prognosis or predicting an outcome for chemotherapeutic drug cancer therapy in a subject, the method comprising the steps of: (a) analyzing a sample from the subject with an assay that distinguishes between valine and alanine at amino acid position 16 of manganese superoxide dismutase or that distinguishes between the codon encoding valine and the codon encoding alanine at amino acid position 16 of manganese superoxide dismutase; and (c) determining the subject's genotype for amino acid position 16 of manganese superoxide dismutase, thereby providing a prognosis for chemotherapeutic drug cancer therapy.

In one embodiment, the chemotherapeutic drug is selected from the group consisting of doxorubicin, cyclophosphamide, and 5-fluorouracil. In one embodiment, the cancer is selected from the group consisting of breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, lymphoma, leukemia, and soft tissue and osteogenic sarcoma. In one embodiment, the cancer is breast cancer. In one embodiment, the sample is from blood, saliva, cheek cells, or tissue biopsy. In one embodiment, the sample is from blood. In one embodiment, the assay is PCR. In one embodiment, the assay is mass spectroscopy. In one embodiment, he assay analyzes DNA in the sample. In one embodiment, the assay analyzes protein in the sample. In one embodiment, the presence of at least one copy of the valine allele predicts a better response to chemotherapeutic drug therapy than the presence of at least one copy of the alanine allele. In one embodiment, the therapy is combination therapy. In one embodiment, the therapy is monotherapy.

In another aspect, the present invention provides a method for providing a prognosis for chemotherapeutic drug cancer therapy in a subject, the method comprising the steps of: (a)

contacting a sample from the subject with a primer set of a first oligonucleotide and a second oligonucleotide that distinguishes between the codon encoding valine and the codon encoding alanine at amino acid position 16 of manganese superoxide dismutase; (b) amplifying nucleic acid in the sample; and (c) determining the subject's genotype for amino acid position 16 of manganese superoxide dismutase, thereby providing a prognosis for chemotherapeutic drug cancer therapy. In another aspect, the chemotherapeutic drug is selected from the group consisting of doxorubicin, cyclophosphamide, and 5-fluorouracil.

In another aspect, the present invention provides a method of providing a prognosis for chemotherapeutic drug cancer therapy in a subject, the method comprising the steps of: (a) contacting a protein sample from the subject with an antibody that distinguishes between valine and alanine at amino acid position 16 of manganese superoxide dismutase; (b) detecting the antibody in the sample; and (c) determining the subject's genotype for amino acid position 16 of manganese superoxide dismutase, thereby providing a prognosis for chemotherapeutic drug cancer therapy. In another aspect, the chemotherapeutic drug is selected from the group consisting of doxorubicin, cyclophosphamide, and 5-fluorouracil.

In another aspect, the present invention provides a method for providing a prognosis for chemotherapeutic drug cancer therapy in a subject, the method comprising the steps of: (a) analyzing a nucleic acid sample from the subject with mass spectroscopy; and (c) determining the subject's genotype for the codon encoding amino acid position 16 of manganese superoxide dismutase, thereby providing a prognosis for chemotherapeutic drug cancer therapy. In another aspect, the chemotherapeutic drug is selected from the group consisting of doxorubicin, cyclophosphamide, and 5-fluorouracil.

In another aspect, the present invention provides a method of providing a prognosis for chemotherapeutic drug cancer therapy in a subject, the method comprising the steps of: (a) analyzing a protein sample from the subject with mass spectroscopy; and (b) determining the subject's genotype for amino acid position 16 of manganese superoxide dismutase, thereby providing a prognosis for chemotherapeutic drug cancer therapy. In another aspect, the chemotherapeutic drug is selected from the group consisting of doxorubicin, cyclophosphamide, and 5-fluorouracil.

In another aspect, the present invention provides a method of providing a prognosis for doxorubicin breast cancer therapy in a subject, the method comprising the steps of: (a) analyzing a sample from the subject with a primer set of a first oligonucleotide and a second oligonucleotide that distinguishes between the codon encoding valine and the codon encoding alanine at amino acid position 16 of manganese superoxide dismutase; (b) amplifying nucleic acid in the sample; and (c) determining the subject's genotype for amino acid position 16 of manganese superoxide dismutase, thereby providing a prognosis for doxorubicin breast cancer therapy.

In another aspect, the present invention provides a method of providing a prognosis for cyclophosphamide breast cancer therapy in a subject, the method comprising the steps of: (a) analyzing a sample from the subject with a primer set of a first oligonucleotide and a second oligonucleotide that distinguishes between the codon encoding valine and the codon encoding alanine at amino acid position 16 of manganese superoxide dismutase; (b) amplifying nucleic acid in the sample; and (c) determining the subject's genotype for amino acid position 16 of manganese superoxide dismutase, thereby providing a prognosis for cyclophosphamide breast cancer therapy.

In another aspect, the present invention provides a method of providing a prognosis for 5-fluorouracil breast cancer therapy in a subject, the method comprising the steps of: (a) analyzing a sample from the subject with a primer set of a first oligonucleotide and a second oligonucleotide that distinguishes between the codon encoding valine and the codon encoding alanine at amino acid position 16 of manganese superoxide dismutase; (b) amplifying nucleic acid in the sample; and (c) determining the subject's genotype for amino acid position 16 of manganese superoxide dismutase, thereby providing a prognosis for 5-fluorouracil breast cancer therapy.

Other objects, features, and advantages of the present invention will be apparent to one of skill in the art from the following detailed description and figures.

BRIEF DESCRIPTION OF THE DRAWINGS

FIG. 1 provides an amino acid and nucleic acid sequence of a manganese superoxide dismutase gene. The polymorphism site is shown in bold and underline.

FIG. 2: Association between the Val16Ala polymorphism and breast cancer survival. Shown are the 10 year Kaplan-Meier survival curves. (a) Combined analysis of the US and Norwegian Cohorts. Cumulative survival of patients by Val16Ala genotype (n=573). Patient survival is significantly associated with the Val16Ala genotype. Log-rank test: P=0.003. (b) US Cohort. Cumulative survival of patients by Val16Ala genotype status (n=244). Log-rank test: P=0.038. (c) Norwegian Cohort. Cumulative survival of patients by Val16Ala genotype (n=329). Log-rank test: P=0.039.

DETAILED DESCRIPTION OF THE INVENTION

I. Introduction

Figure 3A:
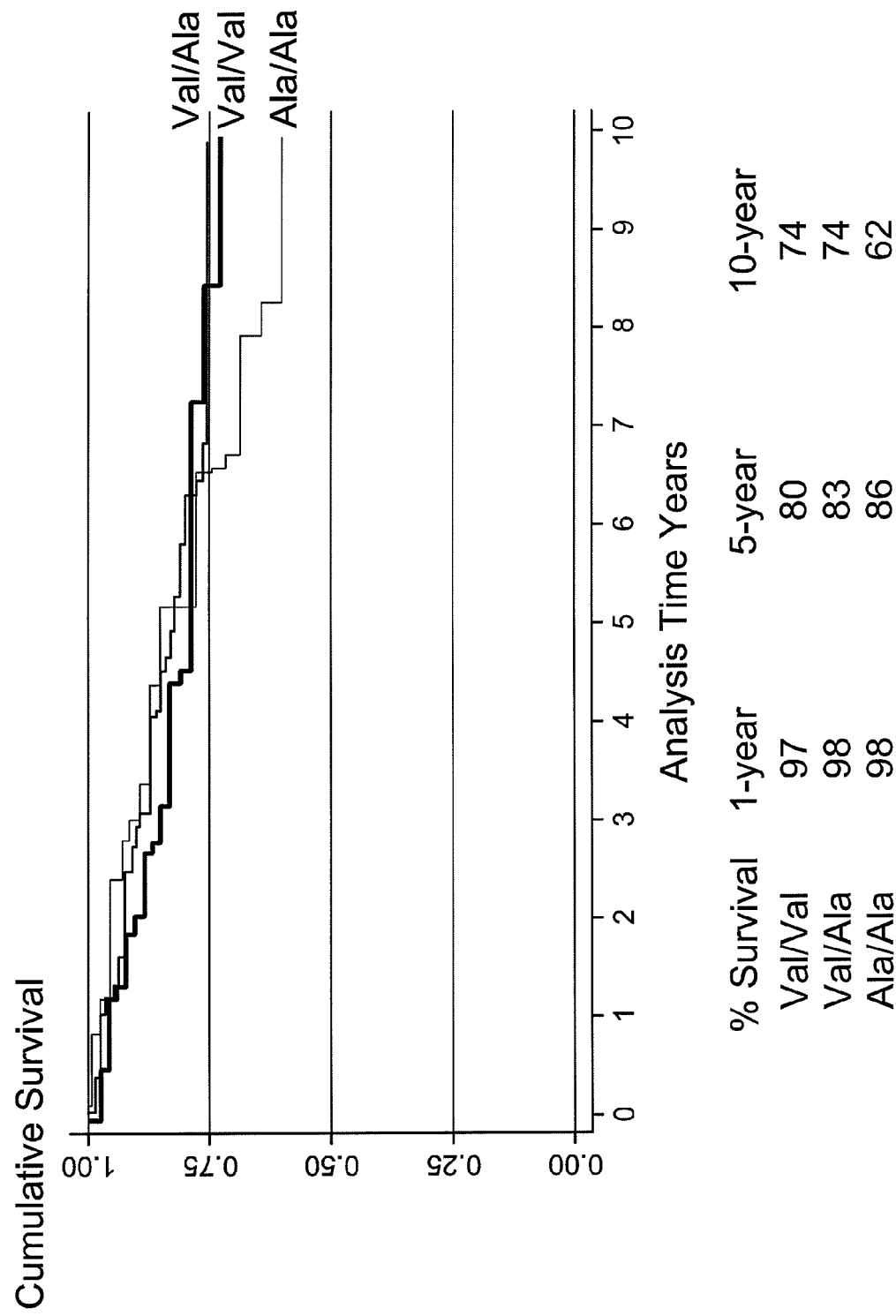
FIG. 3: Association between Val16Ala polymorphism and breast cancer survival in patients after stratification by chemotherapy. Shown are the 10 year Kaplan-Meier survival curves. (A) Cumulative survival of patients not receiving any chemotherapy by Val16Ala genotype status (n=221). The survival of patients who did not receive chemotherapy is not significantly associated with the Val16Ala genotype. Log-rank test: P=0.634. (b) Cumulative survival of patients receiving any chemotherapy by Val16Ala genotype (n=322). There is a significant association between the Val16Ala genotype and breast survival in patients receiving chemotherapy. Log-rank test: P=0.001. (c) Cumulative survival of patients receiving doxorubicin by Val16Ala genotype status (n=160). There is a significant association between the Val16Ala genotype and breast survival in patients receiving doxorubicin-based therapy. Log-rank test: P=0.001. (d) Cumulative survival of patients receiving 5-FU by Val16Ala genotype status (n=121). There is a significant association between the Val16Ala genotype and breast survival in patients receiving 5-FU-based therapy. Log-rank test: P=0.014. (e) Cumulative survival of patients receiving cyclophosphamide by Val16Ala genotype status (n=143). There is a significant association between the Val16Ala genotype and breast survival in patients receiving cyclophosphamide-based therapy. Log-rank test: P<0.001.
Figure 3B:
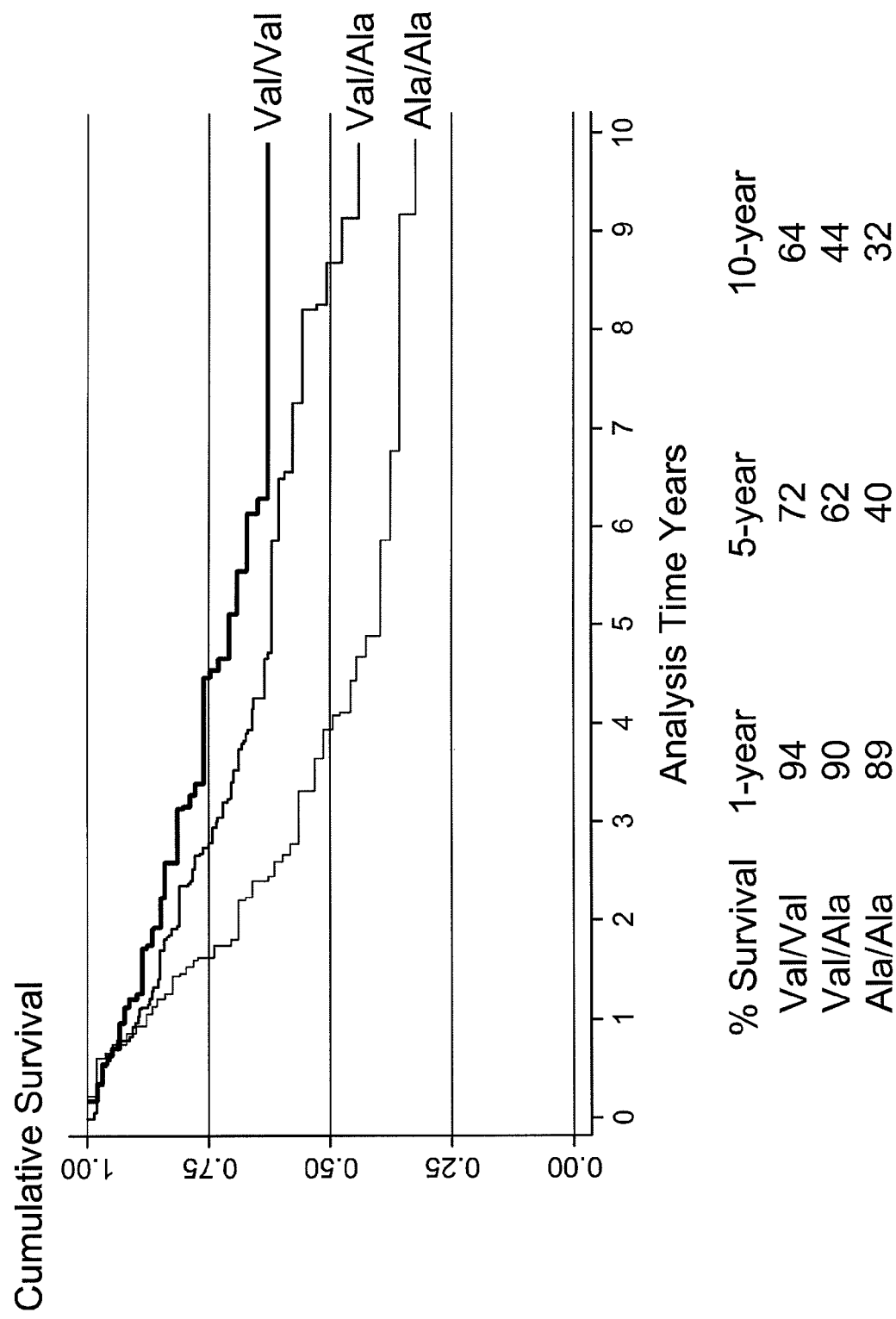
Figure 3C:
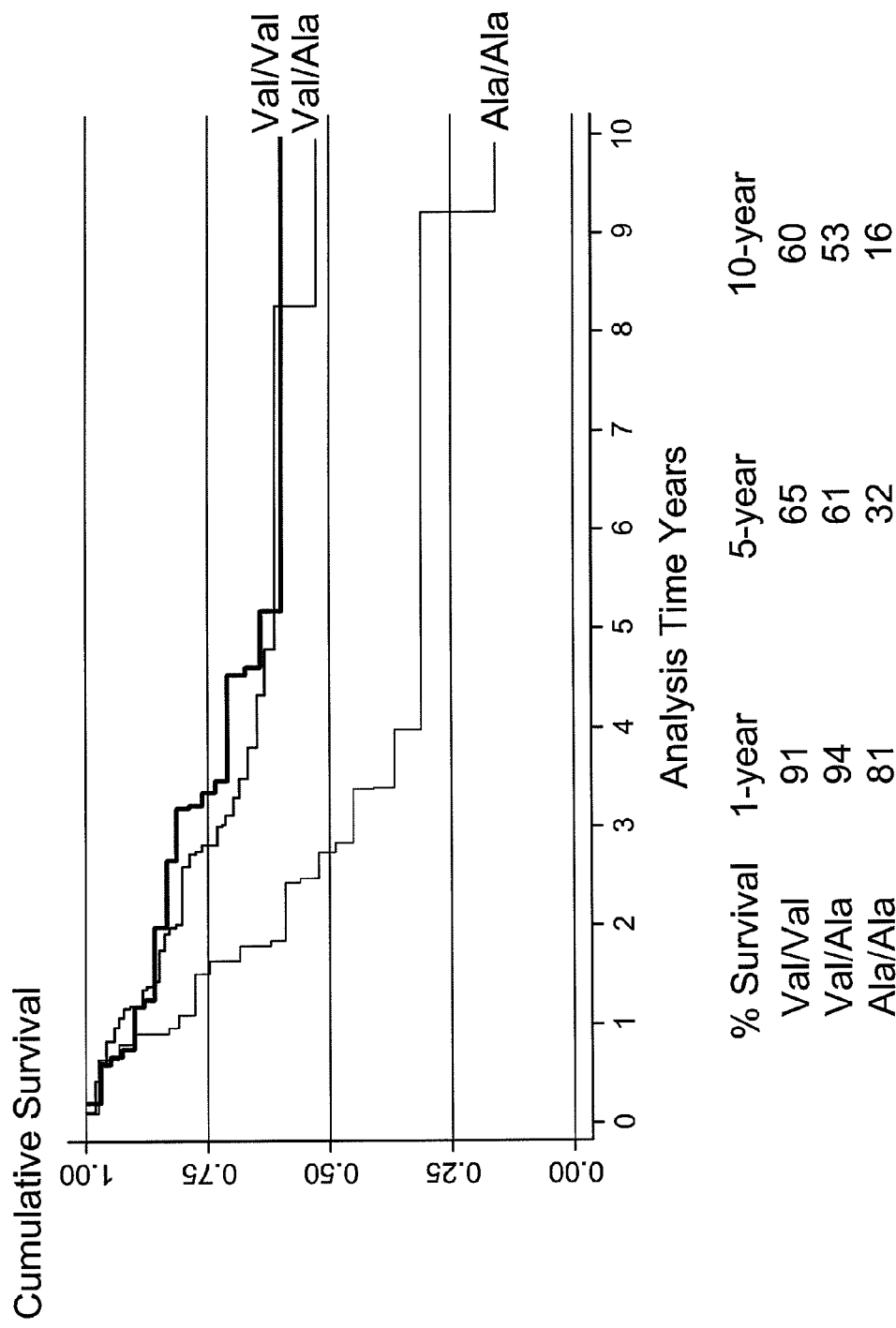
Figure 3E:
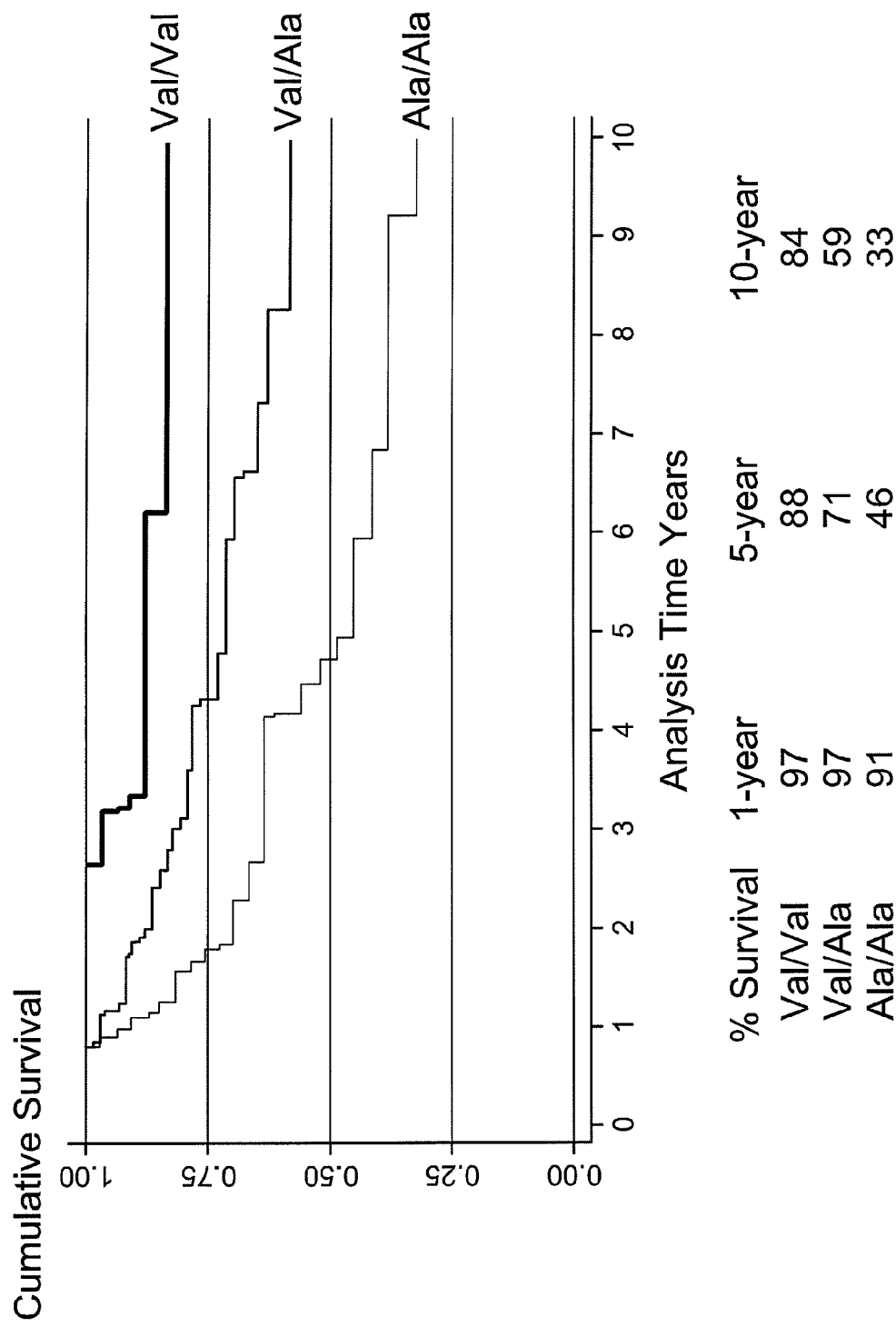
Figure 4:
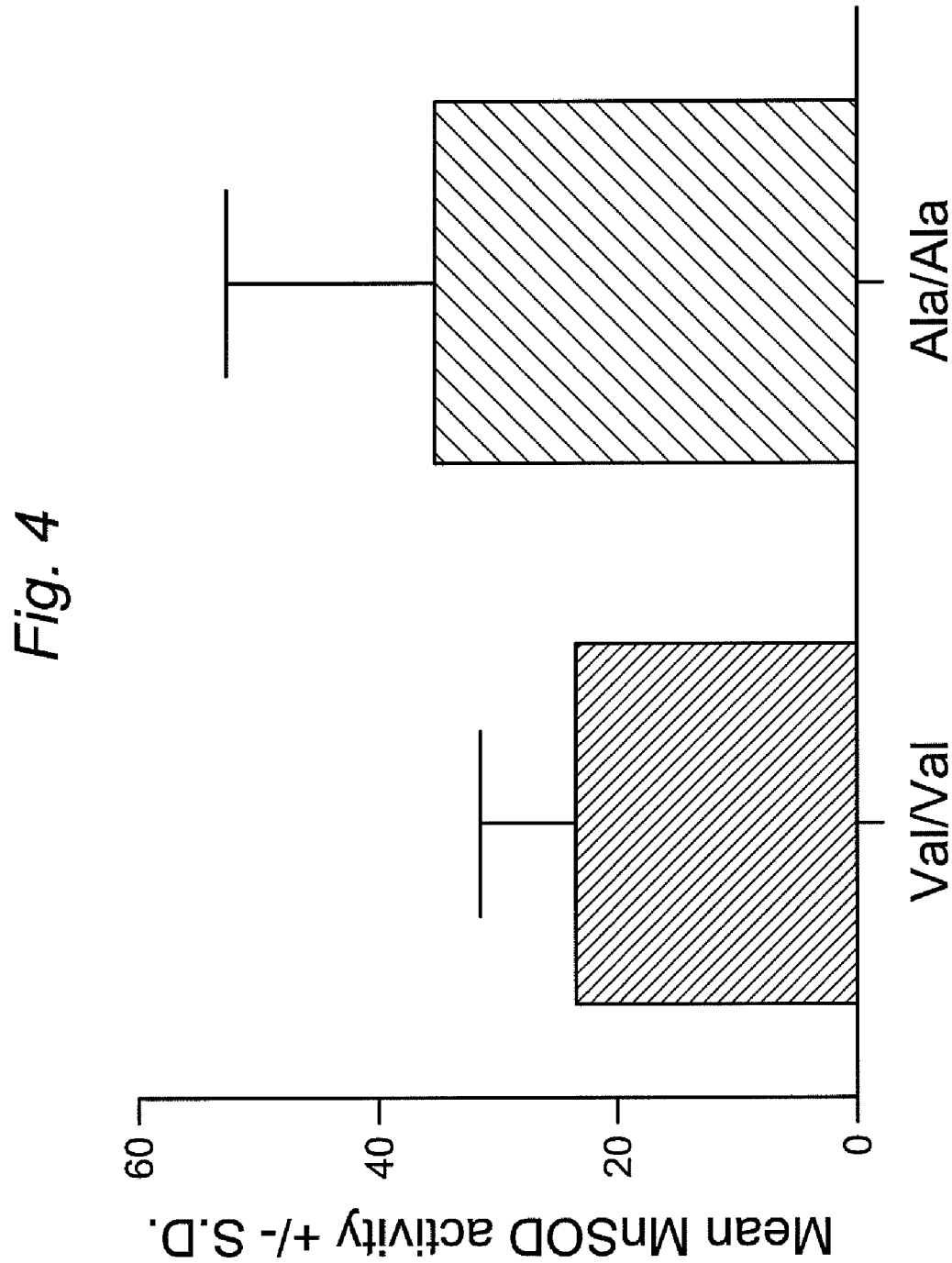
FIG. 4: MnSOD activity in human lymphocytes by Val16Ala genotype. Shown is the mean MnSOD activity±SD for lymphoblastoid cell lines with the Val/Val (n=5) and Ala/Ala (n=5) SOD2 genotypes. Lymphoblastoid cells with the Ala/Ala genotype have a 49% increase in MnSOD activity compared cells that have the Val/Val genotype (P=0.052).

Superoxide dismutase (SOD) catalyzes the destruction of the $O^{2-}$ free radical. It protects oxygen-metabolizing cells against harmful effects of superoxide free-radicals. SOD catalyzes the dismutation of two molecules of superoxide anion into water and hydrogen peroxide. In humans, three forms of superoxide dismutase are present. SOD1 is located in the cytoplasm, SOD2 (or MnSOD) in the mitochondria and SOD3 is extracellular. The first is a dimer (consists of two units), while the others are tetramers (four identical subunits). SOD1 and SOD3 contain copper and zinc, while SOD2 has manganese in its reactive centre. The genes are located on chromosomes 21, 6 and 4, respectively (21q22.1, 6q25.3 and 4p15.3-p15.1).

A common variant of MnSOD is the Val16Ala polymorphism in the mitochondrial targeting sequence, caused by substitution of a T by C, changing the codon from GTT=valine to GCT=alanine) in the nucleic acid sequence (see, e.g., FIG. 1, nucleic acid position 142; Rosenblum et al., *PNAS USA* 93:4471-4473 (1996); also described as the Val-9Ala allele see also Sutton et al., Pharmacogenetics, vol. 13, 145-157, 2003; Sutton et al., Pharmacogenetics and Genomics, vol. 15, 311-319, 2005). About 40% of the population is heterozygous for this allele, with 20% homozygous for each allele. Some studies have shown that the T or Ala allele is associated with an increased risk of breast cancer (Ambrosone et al., *Cancer Res.* 59-602-606 (1999); Mitrunen et al., *Carcinogenesis* 22:827-829 (2001)), while other studies have found no increased breast cancer risk associated with this allele (Egan et al., *Cancer Lett.* 199:27-33 (2003); Tamimi et al., *Cancer Epidemiol. Biomarkers Prev.* 13:989-996 (2004). However, Egan et al. found that the presence of this polymorphism may modify the risk of breast cancer among smokers. Another study showed increased association of the valine allele with breast cancer (Bergman et al., *J. Cancer Res. Clin Oncol.* 131:439-444 (2005). Other studies found no risk association with either gastric cancer or lung cancer risk (see, e.g., Wang et al., *J. Occup. Environ. Med.* 46:556-564 (2004); Martin et al., *J. Surg. Res.* 124:92-87 (2005). Other studies have shown that this polymorphism is associated with cardiomyopathy (Hiroi et al., *Biochem. Biophys. Res. Commun.* 261:332-339 (1999); Valenti et al., *J. Med. Genet.* 41:946-950 (2004), and increased risk of colorectal cancer (Stoehlmacher et al., *Oncol. Rep.* 9:235-238 (2002). Therefore, the significance of the alanine allele and cancer, including breast cancer, is unclear.

In contrast, the present invention demonstrates for the first time that the presence of the Val16Ala allele is predictive of poor prognosis for cancer patients treated with a chemotherapeutic drug. In a study of 70 breast cancer patients treated with doxorubicin, homozygous carriers of the Val/Val genotype showed very good survival. Heterozygous carriers of the Val/Ala genotype showed intermediate survival, while homozygous carriers of the Ala/Ala genotype showed poor survival. In 5-year and 10-year survival studies of patients receiving doxorubicin, cyclophosphamide, or 5-fluorouracil-based chemotherapy, in all therapy groups the Ala/Ala genotype significantly increased the risk of poor outcome. Without being bound to a theory, the data suggests that the MnSOD polymorphism creates resistance to the chemotherapeutic drug.

Determination of the valine or alanine genotype at position 16 is therefore a novel biomarker that predicts response to chemotherapeutic drug therapy in cancer. The present invention therefore provides methods of genotyping this position in MnSOD to determine whether or not chemotherapeutic drug therapy is appropriate. The genotype can be determined by examining either protein (Val or Ala at position 16) or nucleic acid. Any codon encoding valine (GTA, GTC, GTG, GTT) or alanine (GCA, GCC, GCG, GCT) at position 16 can be examined in the nucleic acid (both RNA and protein). In one embodiment, the codon has changed from GTT to GCT. Methods of genotyping include mass spectroscopy, microarrays, PCR, e.g., Taqman assay, FAS-PCR (Howard et al., *BioTechniques* 26:280-281 (1999)), or pyrosequencing (Garcia et al., *Gene* 253:249-257 (2000)). Methods of genotyping also include immunoassays such as ELISA. Any convenient sample can be used, e.g., blood, biopsy tissue, saliva, cheek cells etc.

II. Definitions

As used herein, the following terms have the meanings ascribed to them unless specified otherwise.

"Manganese superoxide dismutase" or "MnSOD" refers to nucleic acids (e.g., gene, pre-mRNA, mRNA), polypeptides, polymorphic variants, alleles, mutants, and interspecies homologs that: (1) have an amino acid sequence that has greater than about 60% amino acid sequence identity, e.g., about 65%, 70%, 75%, 80%, 85%, 90%, 95%, preferably about 91%, 92%, 93%, 94%, 95%, 96%, 97%, 98%, 99%, or greater amino acid sequence identity, preferably over a region of at least about 25, 50, 100, 200, 500, 1000, or more amino acids, to a polypeptide encoded by a referenced nucleic acid or an amino acid sequence described herein (see, e.g., FIG. 1); (2) specifically bind to antibodies (e.g., polyclonal antibodies) raised against an immunogen comprising a referenced amino acid sequence, immunogenic fragments thereof, and conservatively modified variants thereof (3) specifically hybridize under stringent hybridization conditions to a nucleic acid encoding a referenced amino acid sequence, and conservatively modified variants thereof; and/or (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence (see, e.g., FIG. 1). A polynucleotide or polypeptide sequence is typically from a mammal including, but not limited to, primate (e.g., human), rodent (e.g., rat, mouse, hamster), cow, pig, horse, sheep, or any mammal. The nucleic acids and proteins of the present invention include both naturally-occurring and recombinant molecules. Exemplary human protein sequences encoding MnSOD is provided by Accession No. CAA32502, NP_001019637, and NP_001019636; exemplary nucleic acid sequences are provided by Accession Nos. X14322, NM_001024466.1 and NM_001024465.1. Truncated, alternatively spliced, precursor, and mature forms of MnSOD are also included in the foregoing definition. FIG. 1 also provides an exemplary amino acid and nucleic acid sequence. The C to T change is at nucleotide 142 of the nucleic acid sequence in FIG. 1, and the Val to Ala change is at position 16 of the protein in FIG. 1.

"Chemotherapeutic drug" refers to a drug, or a combination of drugs, that kills cancer cells. Examples of different types of chemotherapeutic drugs include, but are not limited to, alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids).

"Doxorubicin" refers to the anthracycline adriamycin and synonyms thereof, including hydroxydaunomycin, hydroxydoxorubicin, Doxil, and Rubex.

"Cyclophosphamide" refers to the nitrogen mustard derivative cytophosphane and synonyms thereof, including Cytoxan and Neosar.

"5-fluorouracil" refers to the pyrimidine antagonist fluorouracil and synonyms thereof, including 5-FU, Adrucil, Fluoroplex, and Efudex.

The term "cancer" refers to human cancers and carcinomas, sarcomas, adenocarcinomas, lymphomas, leukemias, solid and lymphoid cancers, etc. Examples of different types of cancer include, but are not limited to, breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia.

"Chemotherapeutic drug," "doxorubicin," "cyclophosphamide," and "5-fluorouracil"13 sensitive cancer includes, e.g., breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, lymphoma, leukemia, and soft tissue and osteogenic sarcoma.

"Therapeutic treatment" and "cancer therapies" refers to apoptosis-mediated and non-apoptosis mediated cancer therapies including, without limitation, chemotherapy, hormonal therapy, radiotherapy, immunotherapy, and combinations thereof.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "sample" includes sections of tissues such as biopsy and autopsy samples, and frozen sections taken for histological purposes. Such samples include blood and blood fractions or products (e.g., serum, buffy coat, plasma, platelets, red blood cells, and the like), sputum, cheek cells tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally-occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.,* 19:5081 (1991); Ohtsuka et al., *J. Biol. Chem.,* 260:2605-2608 (1985); Rossolini et al., *Mol. Cell. Probes,* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5'-end or at the 3'-end. Polypeptides can be truncated at the N-terminal end or the C-terminal end. Truncated versions of nucleic acid or polypeptide sequences can be naturally-occurring or recombinantly created.

"Polymorphism" refers to the occurrence of two or more genetically determined alternative sequences or alleles in a population. A "polymorphic site" refers to the locus at which divergence occurs. Preferred polymorphic sites have at least two alleles, each occurring at frequency of greater than 1%, and more preferably greater than 10% or 20% of a selected population. A polymorphic locus can be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele and other alleles are designated as alternative or "variant alleles." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

The term "genotype" as used herein broadly refers to the genetic composition of an organism, including, for example, whether a diploid organism is heterozygous or homozygous for one or more variant alleles of interest.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally-occurring amino acid, as well as to naturally-occurring amino acid polymers and non-naturally occurring amino acid polymers.

The term "amino acid" refers to naturally occurring and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, and methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid.

Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

A "label" or "detectable moiety" refers to a composition detectable by spectroscopic, photochemical, biochemical, immunochemical, chemical, or other physical means. For example, a detectable moiety can be coupled either directly or indirectly to the antibodies described herein using methods well known in the art. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), auto-quenched fluorescent compounds that are activated by tumor-associated proteases, enzymes (e.g., luciferase, horseradish peroxidase, alkaline phosphatase, etc.), nanoparticles, electron-dense reagents, biotin, digoxigenin, haptens, and the like.

The term "recombinant," when used with reference, e.g., to a cell, nucleic acid, protein, or vector, indicates that the cell, nucleic acid, protein, or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, overexpressed, underexpressed, or not expressed at all.

The term "heterologous," when used with reference to portions of a nucleic acid, indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

For PCR, a temperature of about 36° C. is typical for low stringency amplification, although annealing temperatures may vary between about 32° C. and about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of about 90-95° C. for about 30 sec-2 min., an annealing phase lasting about 30 sec.-2 min., and an extension phase of about 72° C. for about 1-2 min. Protocols and guidelines for low and high stringency amplification reactions are provided, e.g., in Innis et al. (1990) *PCR Protocols, A Guide to Methods and Applications*, Academic Press, Inc. N.Y.

III. Prognostic Methods

In certain aspects, the present invention provides methods of providing a prognosis for cancer therapy with chemotherapeutic drugs, including cancers such as breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, lymphoma, leukemia, and soft tissue and osteogenic sarcoma. As used herein, the term "providing a prognosis" refers to providing a prediction of the probable course and outcome of chemotherapeutic drug cancer therapy or the likelihood of recovery from the cancer. The methods can also be used to choose a suitable therapy for cancer treatment, e.g., by indicating whether or not the cancer will response well to chemotherapeutic drug treatment.

The MnSOD genotype at amino acid 16 of the subject is measured by taking a blood, saliva, urine, or other tissue sample from a patient and measuring the amount of a polypeptide or polynucleotide of the present invention in the sample using any number of detection methods, such as those discussed herein.

PCR assays such as Taqman® allelic discrimination assay available from Applied Biosystems can be used to discriminate between variants in genomic structure. In another embodiment, mass spectroscopy can be used to detect the MnSOD genotype by analyzing either nucleic acid or protein. Any antibody-based technique for determining a level of expression of a protein of interest can be used to determine the MnSOD genotype. For example, immunoassays such as ELISA, Western blotting, flow cytometry, immunofluorescence, and immunohistochemistry can be used to detect protein in patient samples.

In one embodiment, a blood sample is obtained from a subject, and optionally the buffy coat is prepared from the sample. DNA from the buffy coat is analyzed using PCR (e.g., Taqman) or mass spectroscopy techniques. In some cases, the analysis is automated.

Analysis of the MnSOD genotype, using either protein or nucleic acid can be achieved, for example, by high pressure liquid chromatography (HPLC), alone or in combination with mass spectrometry (e.g., MALDI/MS, MALDI-TOF/MS, tandem MS, etc.).

Analysis of MnSOD genotype can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., Theophilus et al., and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of an nucleic acid marker can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., Methods Mol. Cell. Biol., 3:39-42 (1992)), sequencing with mass spectrometry such as matrix-assisted laser desorption/ionization time-of-flight mass spectrometry (MALDI-TOF/MS; Fu et al., Nature Biotech., 16:381-384 (1998)), and sequencing by hybridization (Chee et al., Science, 274:610-614 (1996); Drmanac et al., Science, 260:1649-1652 (1993); Drmanac et al., Nature Biotech., 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping a subject at a polymorphic site include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., Electrophoresis, 18:2184-93 (1997); Bao, J. Chromatogr. B. Biomed. Sci., 699:463-80 (1997)). Liposome immunoassays, such as flow-injection liposome immunoassays and liposome immunosensors, are also suitable for use in the present invention (see, e.g., Rongen et al., J. Immunol. Methods, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to MnSOD variant protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The genotype analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

The present invention provides compositions, kits, and integrated systems for practicing the assays described herein using the polypeptides or polynucleotides described herein, antibodies specific for the polypeptides or polynucleotides described herein, etc.

IV. Examples

The following examples are offered to illustrate, but not to limit, the claimed invention.

Example 1

Breast cancer survival of 248 breast cancer cases was studied, and it was discovered that the MnSOD Val16Ala allele is significantly associated with breast cancer survival in the study population. (Kaplan-Meier analysis and log-rank test: P=0.005; RR 1.95; 95% CI: 1.27-3.0, P=0.002, in the multivariate Cox analysis with the genotype entered as Val/Val, Val/Ala, Ala/Ala and with adjustments for age at diagnosis, race, TNM stage, estrogen receptor and tumor p53 status). When the population was stratified by doxorubicin treatment (no/yes) it was found that the effect of the MnSOD allele on breast cancer survival was restricted to those patients that received doxorubicin treatment (n=70; Kaplan-Meier analysis and log rank test: P=0.0006; RR 5.63; 95% CI: 1.97-16.1, P=0.001, in the multivariate Cox analysis with the genotype entered as Val/Val, Val/Ala, Ala/Ala). Doxorubicin is often administered in combination with other drugs. In this study, and the patients received various combination treatments of doxorubicin but mostly in combination with cyclophosphamide (AC therapy). Homozygous carriers of the Val/Val genotype showed very good survival with almost no deaths occurring in this group (1 death among 21 patients). Heterozygous carriers had intermediate survival (8 deaths among 38 patients). Homozygous carriers of the Ala/Ala genotype showed very poor survival (6 deaths among 11 patients). The data shows that the MnSOD polymorphism is associated with resistance to doxorubicin therapy. This polymorphism is common in the population and so is a common risk factor for patients that undergo doxorubicin therapy. This allele is a novel biomarker that predicts poor therapeutic response and is applicable for any cancer treated with doxorubicin. Cancer patients should be genotyped for this polymorphism to decide if doxorubicin therapy is appropriate.

Example 2

Breast cancer survival in patents after stratification by chemotherapy was studied, and it was discovered that the MnSOD Val16Ala allele is significantly associated with breast cancer survival in patients receiving chemotherapy. Patients receiving chemotherapy were at a significantly increased risk of poor 10-year survival if they were carriers of the Ala/Ala genotype when compared with carriers of the Val/Val genotype (n=292; HR=2.35; 95% CI: 1.37-4.01). There was an even more significantly increased risk of poor 5-year survival for carriers of the Ala/Ala genotype when compared with carriers of the Val/Val genotype (n=292; HR=2.54; 95% CI: 1.44-4.47).

In a sub-analysis of patients receiving chemotherapy, patients were further stratified by doxorubicin-based, 5-FU-based, and cyclophosphamide-based chemotherapy. In all therapy groups, the Ala/Ala genotype significantly increased the risk of poor outcome in both the 5-year survival analysis and the 10-year survival analysis. Additional modeling of the survival analysis, e.g. using dominant (Val/Val versus Val/Ala and Ala/Ala), recessive (Val/Val and Val/Ala versus Ala/Ala), or additive (Val/Val, Val/Ala, Ala/Ala) models pointed to a recessive effect of the genotype in patients receiving doxorubicin-based therapy and a dominant effect of the genotype in patients receiving either 5-FU-based or cyclophosphamide-based chemotherapy. In the 5-year survival analysis, the most increased risk of poor outcome was seen in carriers of the Ala/Ala genotype who were receiving cyclophosphamide-based therapy (n=124; HR=20.3; 95% CI: 4.43-93.3). Significantly increased risk of poor outcome was also seen in carriers of the Ala/Ala genotype who were receiving 5-FU-based therapy (n=111; HR=7.22; 95% CI: 1.77-29.4) and doxorubicin-based therapy (n=149; HR=3.07; 95% CI: 1.13-8.29). Similarly, in the 10-year survival analysis, the most increased risk of poor outcome was seen in carriers of the Ala/Ala genotype who were receiving cyclophosphamide-based therapy (n=124; HR=22.1; 95% CI: 5.06-96.4). Significantly increased risk of poor outcome was also seen in carriers of the Ala/Ala genotype who were receiving 5-FU-based therapy (n=111; HR=6.85; 95% CI: 1.86-25.3) and doxorubicin-based therapy (n=149; HR=3.16; 95% CI: 1.18-8.51).

TABLE 1

Patient Characteristics[1]

| Tumor Parameter | US Cohort (n = 244) | Norway Cohort (n = 329) | p-value |
|---|---|---|---|
| SOD2-01 | | | |
| Val/Val | 76 (31%) | 75 (23%) | 0.060 |
| Val/Ala | 121 (50%) | 174 (53%) | |
| Ala/Ala | 47 (19%) | 80 (24%) | |
| Race | | | |
| African Descent | 139 (57%) | — | <0.001 |
| European Descent | 105 (43%) | 100 (100%) | |
| Age at diagnosis[2] (Mean ± s.d.) | 55.0 ± 13.9 | 62.5 ± 13.8 | <0.001 |
| Survival | | | |
| Alive | 161 (66%) | 223 (68%) | 0.651 |
| Deceased | 83 (34%) | 106 (32%) | |
| Tumor Size | | | |
| T1 | 53 (27%) | 90 (28%) | <0.001 |
| T2 | 93 (47%) | 95 (30%) | |
| T3 | 41 (21%) | 78 (24%) | |
| T4 | 10 (5%) | 56 (18%) | |
| Node Involvement | | | |
| No | 141 (62%) | 136 (45%) | <0.001 |
| Yes | 85 (38%) | 167 (55%) | |
| Grade | | | |
| 1 | 33 (16%) | 41 (13%) | <0.001 |
| 2 | 74 (35%) | 177 (56%) | |
| 3 | 104 (49%) | 100 (31%) | |
| Estrogen Receptor Status | | | |
| Negative | 100 (41%) | 96 (31%) | 0.011 |
| Positive | 143 (59%) | 216 (69%) | |
| p53 Mutation Status | | | |
| Negative | 198 (81%) | 226 (70%) | 0.002 |
| Positive | 46 (19%) | 98 (30%) | |
| Adjuvant Chemotherapy | | | |
| No | 97 (43%) | 98 (27%) | <0.001 |
| Yes | 130 (57%) | 239 (73%) | |

[1]Chi-square tests were used to compare differences in patient characteristics.
[2]Un-paired student t-test was used to compare differences in the mean age at diagnosis.

TABLE 2

Association of SOD2-01 polymorphism with breast cancer survival

| | Univariate | | Multivariate[1] | |
|---|---|---|---|---|
| | HR (95% CI) | p-value | HR (95% CI) | p-value |
| Meta-analysis | (n = 573) | | (n = 465) | |
| Val/Val | 1 (ref.) | | 1 (ref.) | |
| Val/Ala | 1.27 (0.87-1.84) | 0.215 | 1.26 (0.93-1.91) | 0.274 |
| Ala/Ala | 1.96 (1.30-2.94) | 0.001 | 2.19 (1.40-3.34) | 0.001 |
| Val/Ala & Ala/Ala | 1.47 (1.03-2.08) | 0.034 | 1.52 (1.03-2.24) | 0.033 |
| | $p_{trend}$ | 0.001 | | |
| Val/Val & Val/Ala | 1 (ref.) | | 1 (ref.) | |
| Ala/Ala | 1.67 (1.22-2.27) | 0.001 | 1.91 (1.36-2.67) | <0.001 |
| US Cohort | (n = 244) | | (n = 183) | |
| Val/Val | 1 (ref.) | | 1 (ref.) | |
| Val/Ala | 1.62 (0.93-2.81) | 0.088 | 1.58 (0.84-2.96) | 0.155 |
| Ala/Ala | 2.24 (1.20-4.18) | 0.011 | 2.44 (1.11-5.37) | 0.027 |
| Val/Ala & Ala/Ala | 1.78 (1.05-3.00) | 0.031 | 1.75 (0.96-3.18) | 0.067 |
| | $p_{trend}$ | 0.011 | | |
| Val/Val & Val/Ala | 1 (ref.) | | 1 (ref.) | |
| Ala/Ala | 1.63 (1.00-2.66) | 0.050 | 1.72 (0.96-3.06) | 0.066 |
| Norway Cohort | (n = 329) | | (n = 282) | |
| Val/Val | 1 (ref.) | | 1 (ref.) | |
| Val/Ala | 1.04 (0.62-1.73) | 0.880 | 0.88 (0.49-1.56) | 0.662 |
| Ala/Ala | 1.73 (1.01-2.97) | 0.047 | 1.91 (1.06-3.45) | 0.031 |
| Val/Ala & Ala/Ala | 1.24 (0.77-2.01) | 0.369 | 1.22 (0.73-2.05) | 0.448 |
| | $p_{trend}$ | 0.033 | | |
| Val/Val & Val/Ala | 1 (ref.) | | 1 (ref.) | |
| Ala/Ala | 1.68 (1.12-2.52) | 0.012 | 1.97 (1.29-3.01) | 0.002 |

[1]Cox Proportional-Hazards regression with adjustments for age at diagnosis, cohort, race, tumor size, nodal involvement, tumor grade, estrogen receptor status and p53 mutation.

TABLE 3

Effect of ER and p53 mutation on the association of SOD2-01 with 10 year breast cancer survival

| | Univariate | | Multivariate[1] | |
|---|---|---|---|---|
| | HR (95% CI) | p-value | HR (95% CI) | p-value |
| ER negative | (n = 196) | | (n = 162) | |
| Val/Val | 1 (ref.) | | 1 (ref.) | |
| Val/Ala | 0.97 (0.54-1.74) | 0.907 | 1.11 (0.56-2.20) | 0.760 |
| Ala/Ala | 1.76 (0.93-3.32) | 0.080 | 1.64 (0.83-3.26) | 0.157 |
| Val/Ala & Ala/Ala | 1.18 (0.69-2.04) | 0.563 | 1.24 (0.67-2.29) | 0.487 |
| | $p_{trend}$ | 0.060 | | |
| Val/Val & Val/Ala | 1 (ref.) | | 1 (ref.) | |
| Ala/Ala | 1.84 (1.13-2.98) | 0.014 | 1.77 (1.03-2.99) | 0.035 |
| ER positive | (n = 359) | | (n = 299) | |
| Val/Val | 1 (ref.) | | 1 (ref.) | |
| Val/Ala | 1.54 (0.83-2.55) | 0.095 | 1.45 (0.83-2.24) | 0.192 |
| Ala/Ala | 2.14 (1.24-3.69) | 0.007 | 2.54 (1.35-4.78) | 0.004 |
| Val/Ala & Ala/Ala | 1.73 (1.07-2.78) | 0.024 | 1.76 (1.04-2.99) | 0.035 |
| | $p_{trend}$ | 0.005 | | |
| Val/Val & Val/Ala | 1 (ref.) | | 1 (ref.) | |
| Ala/Ala | 1.60 (1.06-2.41) | 0.024 | 2.06 (1.32-3.21) | 0.001 |
| P53 Mutation Negative | (n = 424) | | (n = 340) | |
| Val/Val | 1 (ref.) | | 1 (ref.) | |
| Val/Ala | 1.38 (0.87-2.20) | 0.171 | 1.63 (0.98-2.73) | 0.060 |
| Ala/Ala | 1.98 (1.20-3.26) | 0.007 | 2.58 (1.50-4.45) | 0.001 |
| Val/Ala & Ala/Ala | 1.58 (1.02-3.43) | 0.039 | 1.90 (1.18-3.05) | 0.008 |
| | $p_{trend}$ | 0.007 | | |
| Val/Val & Val/Ala | 1 (ref.) | | 1 (ref.) | |
| Ala/Ala | 1.60 (1.09-2.35) | 0.017 | 1.89 (1.25-2.85) | 0.002 |
| P53 Mutation Positive | (n = 144) | | (n = 125) | |
| Val/Val | 1 (ref.) | | 1 (ref.) | |
| Val/Ala | 0.82 (0.43-1.59) | 0.547 | 0.76 (0.37-1.56) | 0.458 |
| Ala/Ala | 1.97 (0.95-4.08) | 0.069 | 1.37 (0.58-3.26) | 0.468 |
| Val/Ala & Ala/Ala | 1.04 (0.56-1.95) | 0.915 | 0.89 (0.45-1.76) | 0.734 |
| | $p_{trend}$ | 0.038 | | |

TABLE 3-continued

Effect of ER and p53 mutation on the association of SOD2-01 with 10 year breast cancer survival

|  | Univariate | | Multivariate[1] | |
| --- | --- | --- | --- | --- |
|  | HR (95% CI) | p-value | HR (95% CI) | p-value |
| Val/Val & Val/Ala | 1 (ref.) |  | 1 (ref.) |  |
| Ala/Ala | 2.40 (1.40-4.12) | 0.001 | 1.82 (0.99-3.33) | 0.054 |

[1]Cox Proportional-Hazards regression with adjustments for age at diagnosis, study site, race, tumor size, tumor grade, nodal involvement, estrogen receptor status and p53 mutation.

TABLE 4

Modification of the association of SOD2-01 with 10-year breast cancer survival by receipt of chemotherapy

|  | Univariate | | Multivariate[1] | |
| --- | --- | --- | --- | --- |
|  | HR (95% CI) | p-value | HR (95% CI) | p-value |
| No Chemotherapy | (n = 221) | | (n = 158) | |
| Val/Val | 1 (ref.) |  | 1 (ref.) |  |
| Val/Ala | 0.96 (0.49-1.87) | 0.898 | 1.54 (0.64-3.71) | 0.332 |
| Ala/Ala | 1.31 (0.62-2.75) | 0.480 | 2.23 (0.78-6.37) | 0.134 |
| Val/Ala & Ala/Ala | 1.06 (0.57-1.99) | 0.846 | 1.47 (0.67-3.24) | 0.338 |
|  | $p_{trend}$ | 0.488 | | |
| Val/Val & Val/Ala | 1 (ref.) |  | 1 (ref.) |  |
| Ala/Ala | 1.33 (0.73-2.43) | 0.345 | 2.01 (0.96-4.16) | 0.061 |
| Chemotherapy | (n = 322) | | (n = 292) | |
| Val/Val | 1 (ref.) |  | 1 (ref.) |  |
| Val/Ala | 1.42 (0.90-2.25) | 0.130 | 1.12 (0.69-1.86) | 0.632 |
| Ala/Ala | 2.41 (1.47-3.94) | <0.001 | 2.35 (1.37-4.01) | 0.002 |
| Val/Ala & Ala/Ala | 1.68 (1.09-2.59) | 0.018 | 1.47 (0.93-2.33) | 0.099 |
|  | $p_{trend}$ | 0.001 | | |
| Val/Val & Val/Ala | 1 (ref.) |  | 1 (ref.) |  |
| Ala/Ala | 1.87 (1.29-2.71) | 0.001 | 2.04 (1.37-3.03) | <0.001 |
| Doxorubicin | (n = 160) | | (n = 149) | |
| Val/Val | 1 (ref.) |  | 1 (ref.) |  |
| Val/Ala | 1.13 (0.60-2.10) | 0.709 | 0.83 (0.41-1.64) | 0.583 |
| Ala/Ala | 2.76 (1.41-5.40) | 0.003 | 3.16 (1.18-8.51) | 0.022 |
| Val/Ala & Ala/Ala | 1.50 (0.84-2.68) | 0.169 | 1.09 (0.58-2.04) | 0.785 |
|  | $p_{trend}$ | 0.003 | | |
| Val/Val & Val/Ala | 1 (ref.) |  | 1 (ref.) |  |
| Ala/Ala | 2.57 (1.53-4.35) | <0.001 | 2.44 (1.33-4.47) | 0.004 |
| 5-Fluorouracil | (n = 121) | | (n = 111) | |
| Val/Val | 1 (ref.) |  | 1 (ref.) |  |
| Val/Ala | 2.95 (1.03-8.50) | 0.045 | 2.39 (0.76-7.55) | 0.137 |
| Ala/Ala | 4.63 (1.56-13.72) | 0.006 | 6.85 (1.86-25.3) | 0.004 |
| Val/Ala & Ala/Ala | 3.49 (1.25-9.74) | 0.017 | 3.84 (1.30-11.4) | 0.015 |
|  | $p_{trend}$ | 0.004 | | |
| Val/Val & Val/Ala | 1 (ref.) |  | 1 (ref.) |  |
| Ala/Ala | 1.90 (1.05-3.42) | 0.033 | 2.75 (1.40-5.39) | 0.003 |
| Cyclophosphamide | (n = 143) | | (n = 124) | |
| Val/Val | 1 (ref.) |  | 1 (ref.) |  |
| Val/Ala | 2.82 (1.08-7.36) | 0.035 | 2.02 (0.71-5.72) | 0.185 |
| Ala/Ala | 5.81 (2.17-15.2) | <0.001 | 22.1 (5.06-96.4) | <0.001 |

TABLE 4-continued

Modification of the association of SOD2-01 with 10-year breast cancer survival by receipt of chemotherapy

|  | Univariate | | Multivariate[1] | |
| --- | --- | --- | --- | --- |
|  | HR (95% CI) | p-value | HR (95% CI) | p-value |
| Val/Ala & Ala/Ala | 3.63 (1.44-9.14) | 0.006 | 3.24 (1.23-8.54) | 0.017 |
|  | $p_{trend}$ | <0.001 | | |
| Val/Val & Val/Ala | 1 (ref.) |  | 1 (ref.) |  |
| Ala/Ala | 2.75 (1.56-4.86) | <0.001 | 4.33 (2.18-8.58) | <0.001 |

[1]Cox Proportional-Hazards regression with adjustments for age at diagnosis, study site, race, tumor size, nodal involvement, tumor grade, estrogen receptor status and p53 mutation.

TABLE 5

Modification of the association of SOD2-01 with 5-year breast cancer survival by receipt of chemotherapy

|  | Univariate | | Multivariate[1] | |
| --- | --- | --- | --- | --- |
|  | HR (95% CI) | p-value | HR (95% CI) | p-value |
| No Chemotherapy | (n = 221) | | (n = 158) | |
| Val/Val | 1 (ref.) |  | 1 (ref.) |  |
| Val/Ala | 0.81 (0.38-1.71) | 0.898 | 1.48 (0.55-3.94) | 0.435 |
| Ala/Ala | 0.67 (0.25-1.72) | 0.399 | 0.44 (0.11-1.76) | 0.247 |
| Val/Ala & Ala/Ala | 0.76 (0.37-1.55) | 0.451 | 1.02 (0.40-2.55) | 0.338 |
|  | $p_{trend}$ | 0.390 | | |
| Val/Val & Val/Ala | 1 (ref.) |  | 1 (ref.) |  |
| Ala/Ala | 0.76 (0.33-1.74) | 0.523 | 0.82 (0.30-2.19) | 0.690 |
| Chemotherapy | (n = 322) | | (n = 292) | |
| Val/Val | 1 (ref.) |  | 1 (ref.) |  |
| Val/Ala | 1.42 (0.86-2.32) | 0.167 | 1.15 (0.67-1.98) | 0.604 |
| Ala/Ala | 2.59 (1.53-4.39) | <0.001 | 2.54 (1.44-4.47) | 0.001 |
| Val/Ala & Ala/Ala | 1.74 (1.09-2.77) | 0.020 | 1.55 (0.94-2.54) | 0.085 |
|  | $p_{trend}$ | <0.001 | | |
| Val/Val & Val/Ala | 1 (ref.) |  | 1 (ref.) |  |
| Ala/Ala | 2.03 (1.38-3.00) | <0.001 | 2.19 (1.45-3.31) | <0.001 |
| Doxorubicin | (n = 160) | | (n = 149) | |
| Val/Val | 1 (ref.) |  | 1 (ref.) |  |
| Val/Ala | 1.16 (0.61-2.21) | 0.651 | 0.85 (0.42-1.72) | 0.661 |
| Ala/Ala | 2.78 (1.39-5.56) | 0.004 | 3.07 (1.13-8.29) | 0.027 |
| Val/Ala & Ala/Ala | 1.53 (0.84-2.77) | 0.165 | 1.14 (0.60-2.16) | 0.700 |
|  | $p_{trend}$ | 0.003 | | |
| Val/Val & Val/Ala | 1 (ref.) |  | 1 (ref.) |  |
| Ala/Ala | 2.56 (1.50-4.38) | 0.001 | 2.42 (1.32-4.44) | 0.004 |
| 5-Fluorouracil | (n = 121) | | (n = 111) | |
| Val/Val | 1 (ref.) |  | 1 (ref.) |  |
| Val/Ala | 3.10 (0.92-10.4) | 0.067 | 2.24 (0.61-8.19) | 0.222 |
| Ala/Ala | 5.18 (1.50-17.8) | 0.006 | 7.22 (1.77-29.4) | 0.006 |
| Val/Ala & Ala/Ala | 3.78 (1.16-12.2) | 0.027 | 3.79 (1.11-13.0) | 0.034 |
|  | $p_{trend}$ | 0.005 | | |
| Val/Val & Val/Ala | 1 (ref.) |  | 1 (ref.) |  |
| Ala/Ala | 1.97 (1.05-3.73) | 0.035 | 2.74 (1.32-5.68) | 0.007 |
| Cyclophosphamide | (n = 143) | | (n = 124) | |
| Val/Val | 1 (ref.) |  | 1 (ref.) |  |
| Val/Ala | 2.70 (0.92-7.89) | 0.070 | 1.88 (0.85-6.09) | 0.291 |
| Ala/Ala | 6.13 (2.06-18.3) | 0.001 | 20.3 (4.43-93.3) | <0.001 |
| Val/Ala & Ala/Ala | 3.62 (1.29-10.1) | 0.015 | 3.39 (1.15-9.99) | 0.027 |
|  | $p_{trend}$ | <0.001 | | |

TABLE 5-continued

Modification of the association of SOD2-01 with 5-year breast cancer survival by receipt of chemotherapy

|  | Univariate | | Multivariate[1] | |
|---|---|---|---|---|
|  | HR (95% CI) | p-value | HR (95% CI) | p-value |
| Val/Val & Val/Ala | 1 (ref.) |  | 1 (ref.) |  |
| Ala/Ala | 2.96 (1.59-5.52) | 0.001 | 5.06 (2.39-10.7) | <0.001 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying a subject that is at increased risk for a poor prognosis for chemotherapeutic drug cancer therapy for a cancer selected from the group consisting of breast cancer, prostate cancer, and bladder cancer, wherein the chemotherapeutic drug is selected from the group consisting of an anthracycline, cyclophosphamide, and 5-fluorouracil, the method comprising the steps of:
   (a) analyzing a sample from the subject with an assay that distinguishes between valine and alanine at amino acid position 16 of manganese superoxide dismutase or that distinguishes between the codon encoding valine and the codon encoding alanine at amino acid position 16 of manganese superoxide dismutase; and
   (b) determining the presence of at least one Ala allele in the subject's genotype for the codon encoding amino acid position 16 of manganese superoxide dismutase, thereby identifying that the subject is at increased risk for poor prognosis for chemotherapeutic drug cancer therapy compared to a subject that has a genotype having two Val alleles at the codon encoding amino acid position 16 of manganese superoxide dismutase.

2. The method of claim 1, wherein the cancer is breast cancer.

3. The method of claim 1, wherein the sample is from blood, saliva, cheek cells, or tissue biopsy.

4. The method of claim 1, wherein the sample is from blood.

5. The method of claim 1, wherein the assay is ELISA, Western blotting, flow cytometry, immunofluorescence, immunohistochemistry, mass spectroscopy, PCR, microarray hybridization, RFLP, SSCP, allele specific oligonucleotide hybridization, heteroduplex mobility, thermal cycle sequencing, capillary array sequencing, or solid phase sequencing.

6. The method of claim 1, wherein the assay is PCR.

7. The method of claim 1, wherein the assay is mass spectroscopy.

8. The method of claim 1, wherein the assay analyzes DNA in the sample.

9. The method of claim 8, wherein the assay is mass spectroscopy, PCR, microarray hybridization, RFLP, SSCP, allele specific oligonucleotide hybridization, heteroduplex mobility, thermal cycle sequencing, capillary array sequencing, or solid phase sequencing.

10. The method of claim 1, wherein the assay analyzes protein in the sample.

11. The method of claim 10, wherein the assay is ELISA, Western blotting, flow cytometry, immunofluorescence, immunohistochemistry, or mass spectroscopy.

12. The method of claim 1, wherein the therapy is a combination therapy that comprises cyclophosphamide and/or an anthracycline.

13. The method of claim 1, wherein the therapy is a combination therapy that comprises cyclophosphamide.

14. The method of claim 1, wherein the therapy is monotherapy.

15. A method of identifying a subject that is at increased risk for a poor prognosis for chemotherapeutic drug cancer therapy for breast cancer, wherein the chemotherapeutic drug is selected from the group consisting of an anthracycline, cyclophosphamide, and 5-fluorouracil, the method comprising the steps of:
   (a) amplifying a nucleic acid in the sample that comprises the codon encoding position 16 of manganese superoxide dismutase;

(b) contacting the nucleic acid comprising the codon with an oligonucleotide that distinguishes between the codon encoding valine and the codon encoding alanine at amino acid position 16 of manganese superoxide dismutase;

(c) determining the presence of at least one Ala allele in the subject's genotype for amino acid position 16 of manganese superoxide dismutase, thereby identifying that the subject has a poor prognosis for chemotherapeutic drug cancer therapy for breast cancer compared to a subject that has two Val alleles in the genotype for amino acid position 16 of manganese superoxide dismutase.

16. The method of claim 15, wherein the method comprises a Taqman assay or an RT-PCR assay.

17. A method of identifying a subject that is at increased risk for a poor prognosis for chemotherapeutic drug cancer therapy for breast cancer, wherein the chemotherapeutic drug is selected from the group consisting of an anthracycline, cyclophosphamide, and 5-fluorouracil, the method comprising the steps of:

(a) contacting a protein sample from the subject with an antibody that distinguishes between valine and alanine at amino acid position 16 of manganese superoxide dismutase;

(b) detecting the antibody in the sample; and (c) determining the presence of an Ala at amino acid position 16 of manganese superoxide dismutase, thereby identifying that the subject has a poor prognosis for chemotherapeutic drug cancer therapy for breast cancer compared to a subject that has only Val at amino acid position 16 of manganese superoxide dismutase.

18. A method of identifying a subject that is at increased risk for a poor prognosis for chemotherapeutic drug cancer therapy for breast cancer, wherein the chemotherapeutic drug is selected from the group consisting of an anthracycline, cyclophosphamide, and 5-fluorouracil, the method comprising the steps of:

(a) analyzing a nucleic acid sample from the subject with mass spectroscopy; and (b) determining the presence of at least one Ala allele in the subject's genotype for amino acid position 16 of manganese superoxide dismutase, thereby identifying that the subject has a poor prognosis for chemotherapeutic drug cancer therapy for breast cancer compared to a subject that has two Val alleles in the genotype for amino acid position 16 of manganese superoxide dismutase.

19. A method of identifying a subject that is at increased risk for a poor prognosis for chemotherapeutic drug cancer therapy for breast cancer, wherein the chemotherapeutic drug is selected from the group consisting of an anthracycline, cyclophosphamide, and 5-fluorouracil, the method comprising the steps of:

(a) analyzing a protein sample from the subject with mass spectroscopy; and (b) determining the presence of an Ala at amino acid position 16 of manganese superoxide dismutase, thereby identifying that the subject has a poor prognosis for chemotherapeutic drug cancer therapy for breast cancer compared to a subject that has only Val at amino acid position 16 of manganese superoxide dismutase.

20. A method of identifying a subject at risk for a poor prognosis for anthracycline breast cancer therapy in a subject, the method comprising the steps of:

(a) amplifying a nucleic acid in the sample that comprises the codon encoding position 16 of manganese superoxide dismutase;

(b) contacting the nucleic acid with an oligonucleotide that distinguishes between the codon encoding valine and the codon encoding alanine at amino acid position 16 of manganese superoxide dismutase; and (c) determining the presence of at least one codon encoding an Ala allele in the subject's genotype for amino acid position 16 of manganese superoxide dismutase, thereby identifying that the subject has a poor prognosis for anthracycline breast cancer therapy compared to a patient that has two Val allele at the codon encoding position 16 of manganese superoxice dismutase.

21. A method of identifying a subject at risk for a poor prognosis for cyclophosphamide breast cancer therapy in a subject, the method comprising the steps of:

(a) amplifying a nucleic acid in the sample that comprises the codon encoding position 16 of manganese superoxide dismutase;

(b) contacting the nucleic acid with an oligonucleotide that distinguishes between the codon encoding valine and the codon encoding alanine at amino acid position 16 of manganese superoxide dismutase; and (c) determining the presence of at least one codon encoding an Ala allele in the subject's genotype for amino acid position 16 of manganese superoxide dismutase, thereby identifying that the subject has a poor prognosis for cyclophosphamide breast cancer therapy compared to a patient that has two Val allele at the codon encoding position 16 of manganese superoxice dismutase.

22. A method of identifying a subject at risk for a poor prognosis for 5-fluorouracil breast cancer therapy in a subject, the method comprising the steps of:

(a) amplifying a nucleic acid in the sample that comprises the codon encoding position 16 of manganese superoxide dismutase;

(b) contacting the nucleic acid with an oligonucleotide that distinguishes between the codon encoding valine and the codon encoding alanine at amino acid position 16 of manganese superoxide dismutase; and (c) determining the presence of at least one codon encoding an Ala allele in the subject's genotype for amino acid position 16 of manganese superoxide dismutase, thereby identifying that the subject has a poor prognosis for 5-fluorouracil breast cancer therapy compared to a patient that has two Val allele at the codon encoding position 16 of manganese superoxice dismutase.

* * * * *

UNITED STATES PATENT AND TRADEMARK OFFICE
Certificate

Patent No. 7,985,561 B2                                                            Patented: July 26, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Stefan Ambs, Silver Spring, MD (US); Brenda Boersma, Hagerstown, MD (US); and Sharon Glynn, Ballina (IE).

Signed and Sealed this Twenty-eighth Day of February 2012.

<div style="text-align:right">

MISOOK YU
*Supervisory Patent Examiner*
Art Unit 1642
Technology Center 1600

</div>

UNITED STATES PATENT AND TRADEMARK OFFICE
CERTIFICATE OF CORRECTION

| | |
|---|---|
| PATENT NO. | : 7,985,561 B2 |
| APPLICATION NO. | : 12/268655 |
| DATED | : July 26, 2011 |
| INVENTOR(S) | : Ambs et al. |

It is certified that error appears in the above-identified patent and that said Letters Patent is hereby corrected as shown below:

on the title page, at item (63) Related U.S. Application Data:

change the priority application No. to read -- PCT/US2007/068588 --

Signed and Sealed this
Twenty-fifth Day of September, 2012

David J. Kappos
*Director of the United States Patent and Trademark Office*

SEQUENCE LISTING

```
<160> NUMBER OF SEQ ID NOS: 2

<210> SEQ ID NO 1
<211> LENGTH: 977
<212> TYPE: DNA
<213> ORGANISM: Homo sapiens
<220> FEATURE:
<221> NAME/KEY: misc_feature
<223> OTHER INFORMATION: manganese superoxide dismutase (MnSOD, SOD2)

<400> SEQUENCE: 1
ccgccggcgc gcaggagcgg cactcgtggc tgtggtggct tcggcagcgg cttcagcaga      60
tcggcggcat cagcggtacg accagcacta gcagcatgtt gagccgggca gtgtgcggca     120
ccagcaggca gctggctccg gctttggggt atctgggctc caggcagaag cacagcctcc     180
ccgacctgcc ctacgactac ggcgccctgg aacctcacat caacgcgcag atcatgcagc     240
tgcaccacag caagcaccac gcggcctacg tgaacaacct gaacgtcacc gaggagaagt     300
accaggaggc gttggcaaag ggagatgtta cagcccagac agctcttcag cctgcactga     360
agttcaatgg tggtggtcat atcaatcata gcattttctg gacaaacctc agccctaacg     420
gtggtggaga acccaaaggg gagttgctgg aagccatcaa acgtgacttt ggttcctttg     480
acaagtttaa ggagaagctg acggctgcat ctgttggtgt ccaaggctca ggttggggtt     540
ggcttggttt caataaggaa cggggacact tacaaattgc tgcttgtcca aatcaggatc     600
cactgcaagg aacaacaggc cttattccac tgctggggat tgatgtgtgg gagcacgctt     660
actaccttca gtataaaaat gtcaggcctg attatctaaa agctatttgg aatgtaatca     720
actgggagaa tgtaactgaa agatacatgg cttgcaaaaa gtaaaccacg atcgttatgc     780
tgagtatgtt aagctctttta tgactgtttt tgtagtggta tagagtactg cagaatacag     840
taagctgctc tattgtagca tttcttgatg ttgcttagtc acttatttca taaacaactt     900
aatgttctga ataatttctt actaaacatt ttgttattgg gcaagtgatt gaaaatagta     960
aatgctttgt gtgattg                                                    977

<210> SEQ ID NO 2
<211> LENGTH: 222
<212> TYPE: PRT
<213> ORGANISM: Homo sapiens
<220> FEATURE:
<221> NAME/KEY: MISC_FEATURE
<223> OTHER INFORMATION: manganese superoxide dismutase (MnSOD, SOD2)

<400> SEQUENCE: 2

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
```

```
                    20                      25                      30
Tyr Asp Tyr Gly Ala Leu Glu Pro His Ile Asn Ala Gln Ile Met Gln
        35                      40                      45

Leu His His Ser Lys His His Ala Ala Tyr Val Asn Asn Leu Asn Val
        50                      55                      60

Thr Glu Glu Lys Tyr Gln Glu Ala Leu Ala Lys Gly Asp Val Thr Ala
65                      70                      75                  80

Gln Thr Ala Leu Gln Pro Ala Leu Lys Phe Asn Gly Gly Gly His Ile
                85                      90                      95

Asn His Ser Ile Phe Trp Thr Asn Leu Ser Pro Asn Gly Gly Gly Glu
                100                     105                     110

Pro Lys Gly Glu Leu Leu Glu Ala Ile Lys Arg Asp Phe Gly Ser Phe
            115                     120                     125

Asp Lys Phe Lys Glu Lys Leu Thr Ala Ala Ser Val Gly Val Gln Gly
        130                     135                     140

Ser Gly Trp Gly Trp Leu Gly Phe Asn Lys Glu Arg Gly His Leu Gln
145                     150                     155                 160

Ile Ala Ala Cys Pro Asn Gln Asp Pro Leu Gln Gly Thr Thr Gly Leu
                165                     170                     175

Ile Pro Leu Leu Gly Ile Asp Val Trp Glu His Ala Tyr Tyr Leu Gln
                180                     185                     190

Tyr Lys Asn Val Arg Pro Asp Tyr Leu Lys Ala Ile Trp Asn Val Ile
        195                     200                     205

Asn Trp Glu Asn Val Thr Glu Arg Tyr Met Ala Cys Lys Lys
    210                     215                     220
```